United States Patent [19]

Kleschick

[11] Patent Number: 4,515,956
[45] Date of Patent: May 7, 1985

[54] SELECTIVE PREPARATION OF ISOMERS AND ENANTIOMERS OF CYCLOPROPANE CARBOXYLIC ACIDS

[75] Inventor: William A. Kleschick, Concord, Calif.

[73] Assignee: The Dow Chemical Company, Midland, Mich.

[21] Appl. No.: 639,768

[22] Filed: Aug. 13, 1984

Related U.S. Application Data

[62] Division of Ser. No. 450,500, Dec. 16, 1982, Pat. No. 4,479,005.

[51] Int. Cl.$^3$ .................. C07D 263/24; C07D 263/26
[52] U.S. Cl. .................................................. 548/230
[58] Field of Search ......................................... 548/230

[56] References Cited

U.S. PATENT DOCUMENTS

| | | | |
|---|---|---|---|
| 3,935,280 | 1/1976 | Lane | 548/570 |
| 3,961,070 | 6/1976 | Davis et al. | 424/304 |
| 3,979,519 | 9/1976 | Punja | 424/304 |
| 4,163,787 | 8/1979 | Malhotra et al. | 424/263 |
| 4,256,893 | 3/1981 | Malhotra et al. | 546/301 |
| 4,281,133 | 7/1981 | Malhotra et al. | 424/266 |
| 4,301,154 | 11/1981 | Larson | 424/263 |
| 4,332,815 | 6/1982 | Engel | 424/274 |

Primary Examiner—Paul M. Coughlan, Jr.
Assistant Examiner—S. A. Gibson
Attorney, Agent, or Firm—Michael L. Glenn

[57] ABSTRACT

A process has been discovered for selective preparation of isomers and enantiomers of 2,2-dimethyl-3-(2,2-dihalovinyl)cyclopropane carboxylic acids. In this process an adduct of an alkyl 3,3-dimethyl-4-pentenoate and a substituted 2-oxazolidone is reacted with a substituted dihalomethane compound. The resulting compound is cyclized, dehydrohalogenated and hydrolyzed to yield the desired product. These cyclopropane carboxylic acids are useful precursors for pyrethroid insecticides.

17 Claims, No Drawings

SELECTIVE PREPARATION OF ISOMERS AND ENANTIOMERS OF CYCLOPROPANE CARBOXYLIC ACIDS

CROSS REFERENCE TO RELATED APPLICATION

This is a division of application Ser. No. 450,500 filed Dec. 16, 1982 now U.S. Pat. No. 4,479,005.

BACKGROUND OF THE INVENTION

This invention relates to a process for selectively preparing the cis-isomer of 2,2-dimethyl-3-(2,2-dihalovinyl)cyclopropane carboxylic acid. Novel intermediates useful in the preparation of this isomer are also described.

The 2,2-dimethyl-3-(2,2-dihalovinyl)cyclopropane carboxylic acids (hereafter, DHCA) are well known compounds. These compounds are recognized to be useful intermediates in the preparation of a variety of esters having insecticidal activity.

3-(Fluorophenoxy)benzyl substituted cyclopropanecarboxylates are taught in German Pat. No. 2,547,534. 3-Phenoxybenzyl cyclopropane carboxylates are also taught in Japanese Pat. No. 76-011106. Phenoxy phenyl substituted cyclopropanecarboxylates are described in U.S. Pat. No. 3,961,070 and in South African Pat. No. 75/03,211 (based on U.S. patent application Ser. No. 487,417 filed Oct. 7, 1974). Other related substituted phenyl esters of cyclopropane carboxylic acids are taught in French Pat. No. 2,281,918. Various insecticidal 3-(dihalovinyloxy)benzyl esters of cyclopropanecarboxylic acid are taught in German Pat. No. 2,554,883. In addition, U.S. Pat. No. 3,979,519 teaches the use of 3-(2,2-dihalovinyloxy)benzyl 2-(2,2-dihalovinyl)3,3-dialkylcyclopropane carboxylates as insecticides. Additional esters of DHCA are described in U.S. Pat. Nos. 4,281,133, 4,301,154, 4,256,893, 4,332,815 and 4,163,787. The relevant portions of all of the aforementioned patents are incorporated herein by reference.

The dihalovinyl moiety and carboxylic acid group present on adjacent carbons of the cyclopropane of DHCA can be disposed in cis- or trans-isomeric forms. It is known that certain insecticides prepared from DHCA exhibit increased insecticidal activity relative to certain target species where present as the cis-isomer rather than the trans-isomer or a mixture of isomers. See, Synthetic Pyrethroids, ACS Symposium Series 42, p. 53 (1977). Accordingly, techniques for selectively preparing the cis-isomer of DHCA are of considerable interest.

SUMMARY OF THE INVENTION

In accordance with this invention, the cis-isomer of DHCA or esters thereof, which correspond to the formula I

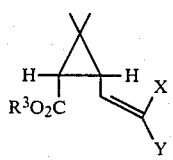

(I)

wherein $R^3$ is hydrogen or $C_1$ to $C_4$ alkyl, X and Y are each independently moieties which when present on an ester derived from or corresponding to Compound I said ester displays significant insecticidal activity. The process for preparing a compound of formula I comprises the steps of:

(a) contacting at reactive conditions a compound corresponding to formula II

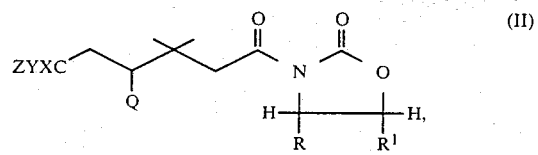

(II)

wherein X and Y are as defined hereinbefore, Q and Z are each independently —Br or —Cl and R and $R^1$ are each independently hydrogen, $C_1$ to $C_4$ alkyl, phenyl or —$CH_2CH_2SCH_3$, with a cyclizing reagent so as to prepare a mixture of compounds corresponding to formulae III (cis-isomer) and IV (trans-isomer)

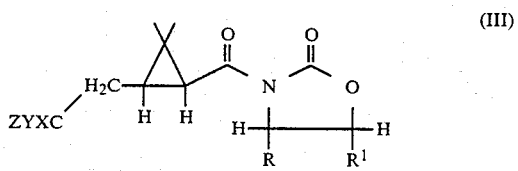

(III)

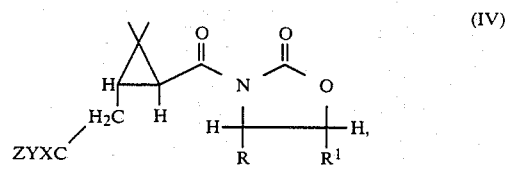

(IV)

wherein the ratio of Compound III to Compound IV is at least 3:1; and (b) Reacting compound III in a liquid mixture so as to prepare a compound corresponding to formula I. Generally, a base will react with compound III to prepare compound 1. Compound I, as noted hereinbefore, is useful in the preparation of a variety of insecticidal compounds.

Compounds II, III and IV are useful intermediates for preparing pyrethroid insecticides and are believed novel compounds. Insecticidal esters derived from Compound IV are active although not as active as those derived from Compound III. Also believed novel is a compound corresponding to formula V

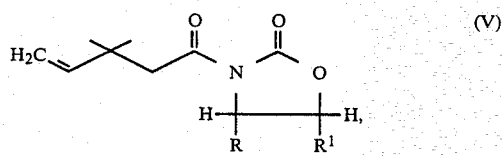

(V)

which is useful as a precursor of certain compounds of formula II.

It should be noted that because of the stereochemistry of the compounds represented by formulae I–VI, these formulae may each encompass two or more enantiomers or diastereomers. All of the formulae drawn herein are depicted to show specific orientation of substituents via standard techniques, where this is intended. In several instances the orientation of a substituent is intentionally made ambiguous to include either of two or more stereoisomers and mixtures of these stereoisomers. For example, in the case of the moieties corresponding to the following formulae

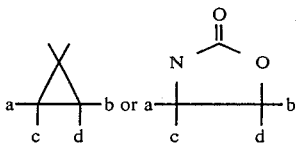

substituents "a" and "b" are oriented cis relative to each other and substituents "c" and "d" are also depicted in a cis orientation. However, these formulae are intended to encompass both of the following possible stereoisomers:

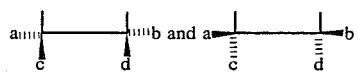

Likewise, the moiety depicted by

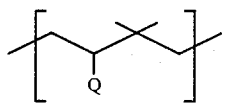

is intended to represent both

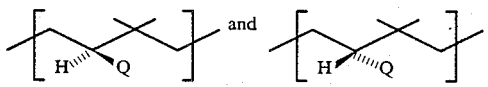

DETAILED DESCRIPTION OF THE INVENTION

A wide variety of esters of DHCA are recognized to display insecticidal activity. A catalog of suitable ester moieties is presented in U.S. Pat. No. 4,332,815 and other patents incorporated herein by reference. A variety of suitable substituents on the vinyl groups of Compound I, i.e., X and Y are also well-known. For example, X and Y can each independently represent halo, $C_1$ to $C_4$ alkyl, $C_2$ to $C_4$ alkenyl, —CN, $C_1$ to $C_4$ perhaloalkyl, benzyl, phenyl, —SR", —$CO_2R$", and —$CONR''_2$, wherein R" at each occurrence is independently a $C_1$ to $C_4$ alkyl. The term halo, as used herein, refers to Br, Cl or F. The moieties X and Y together with the carbon atom to which they are bonded can also form cycloalkyl groups, such as cyclopentylidine or halogenated cyclopentylidine and heterocyclic groups, such as

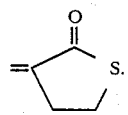

Of particular interest are compounds of formula I wherein X and Y represent one of the following pairs:

| X | Y |
|---|---|
| Cl | Cl |
| Br | Br |
| F | F |
| Cl | $CF_3$ |
| $CH_3$ | Cl |
| $CF_3$ | $CF_3$ |
| $CH_3$ | $CH_3$ |
| —CN | —CN |
| —CN | —COOR" |
| —CN | Cl |
| —$SCH_3$ | —$SCH_3$ |

Preferably, at least one of X or Y is halo or $C_1$ to $C_4$ perhaloalkyl, more preferably halo. Preferably, if only one of X and Y is halo or perhaloalkyl, the other group is alkyl, —CN, —$CO_2R$" or —$CONR''_2$ (wherein R" is as defined hereinbefore). Especially preferred are compounds in which X and Y are each independently halo or trifluoromethyl. Particularly preferred are the compounds in which X and Y are both Cl or Br. Of course, X and Y in formulae II, III and IV will represent the same moieties as in formula I.

Compound V

The compound of formula V is conveniently prepared from an alkyl 3,3-dimethyl-4-pentenoate, which are known compounds. Nakada, Yasuo et al, Bull. Chem. Soc. Jpn., 52 (5), pp. 1511–14 (1979), employed an ethyl 3,3-dimethyl-4-pentenoate to prepare chrysanthemate derivatives. Conveniently, the compound of formula V is prepared by reacting a 3,3-dimethyl-4-pentenoate ester or an acid chloride thereof with a 2-oxazolidone of the formula VI

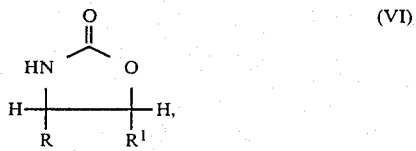

which has preferably first been reacted with a stoichiometric amount of a strong base. The oxazolidone is conveniently prepared by the reaction of an aminoalcohol corresponding to formulae VIIa, VIIb or a mixture thereof

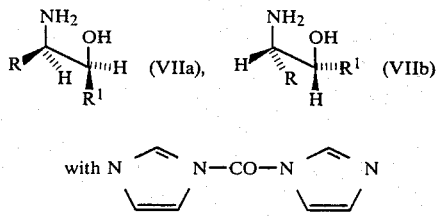

or some other suitable reagent in an inert liquid medium. It is noteworthy that where R and $R^1$ are not both —H, the aminoalcohol of formulae VIIa and VIIb will be optical isomers. The aminoalcohol of formulae VIIa or VIIb can be prepared by known methods from the corresponding resolved amino acids. See, e.g., U.S. Pat. No. 3,935,280. A resolved optical isomer of the amino acid can be obtained commercially or by resolution of a racemic mixture in accordance with known techniques. See, e.g., Greenstein et al, Chemistry of Amino Acids, Vol. 1, Chapter 9, Wiley (1961).

Where the oxazolidone is obtained from an aminoalcohol or an amino acid precursor of the alcohol, the identity of both R and $R^1$ and their orientation in formulae II, III, IV, V and VI will be determined by the starting material employed. Preferably, $R^1$ is —H and R is $C_1$ to $C_4$ alkyl.

From the compound VIIa, the oxazolidone corresponding to the formula:

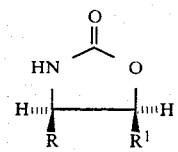
(VIa)

is made. In general, the compound corresponding to formula VIa is preferred over its enantiomer.

Examples of preferred moieties for R and $R^1$ and the corresponding starting materials follow:

| R | $R^1$ | Starting Material |
|---|---|---|
| —$CH_3$ | H | D-alanine |
| —CH—$(CH_3)_2$ | H | D-valine |
| —CH—$CH_2$—$CH_3$<br>\|<br>$CH_3$ | H | D-isoleucine |
| —$CH_2$—CH—$(CH_3)_2$ | H | D-leucine |
| —$CH_2$—$CH_2$—S—$CH_3$ | H | D-methionine |
| —$CH_2$ | H | D-phenylalanine |
| —$CH_2$—$CH_3$ | H | (R)-2-aminobutanol |
| —$CH_3$ | -Phenyl | (1S,2R)-Norephedrine |
| -Phenyl | H | (R)-α-phenyl glycinol |

Compound II

The compound of formula II is in general readily prepared by reacting a compound of formula V with the compound, CXYZQ, wherein X, Y, Z and Q are as described hereinbefore. Compounds of the formula CXYZQ are generally available commercially or can be prepared by known methods. The reaction of haloalkanes (such as CXYZQ) with organic compounds bearing vinyl moieties using transition metal halide catalyst or other activators is well-known. See, e.g. Nakada, Yasuo et al, Bull. Chem. Soc. Jpn., 52 (5), pp. 1511–1514 (1979). Reaction of CXYZQ with the compound of formula V generally proceeds in accordance with these known reactions, although optimal reaction conditions will vary with the lability of the specific CXYZQ reactant. The reaction to prepare Compound II is conveniently conducted neat using an excess of CXYZQ as a diluent at a temperature in the range from about 20° C. to reflux temperatures and an $FeCl_3$ catalyst. Where R and R' are not both hydrogen, the product formed is a mixture of diastereomers of formula II with the carbon atom bearing Q being one asymmetric center. If Q and Z are not the same, an isomeric mixture of products will be produced provided both Q and Z are good "leaving groups".

Step (a)

The cyclization reaction performed in step (a) is one of a type known in the art. The reagents used to induce cyclization are likewise known. See, e.g., Nakada, Yasuo et al, supra. In general bases, in particular protic bases, can be used as cyclizing reagents. For example, alkali metal alkoxides, alkali metal amides, alkyl-substituted alkali metal amides, alkali metal hydrides or alkali metal hydroxides employed in conjunction with phase transfer catalysts. Preferred cyclizing reagents include sodium hydride, potassium hydride, sodium or potassium salts of $C_1$ to $C_4$ alkanols and sodium or potassium carbonate.

A polar diluent essentially inert in the reaction is advantageously employed in this reaction. Preferred diluents include dialkyl ethers, halogenated alkanes, aromatic hydrocarbons, tetrahydrofuran and other cyclic ethers, N-methylpyrrolidone, N,N-dimethylformamide and mixtures thereof. In general, tetrahydrofuran is the solvent of choice. The reaction mixture is preferably essentially anhydrous to avoid undesirable hydrolysis. However, it is possible in a less preferred embodiment of this invention to conduct steps (a) and (b) contemporaneously in a basic aqueous medium. In general, the yield from a reaction in which steps (a) and (b) are conducted concurrently will be somewhat lower than if the two steps are conducted separately using preferred reagents and conditions for each step.

The concentration of Compound II in the diluent is not generally critical. Typically, concentrations of from about 0.1 to about 1 molar are convenient. A slight stoichiometric excess of the cyclizing reagent relative to Compound II is advantageously employed to promote complete reaction.

The reaction temperature is not critical so long as a practical reaction rate is maintained without any substantial deleterious affect on the product or reactants. Temperatures in the range from about 0° C. to temperatures at which refluxing occurs are generally convenient and advantageous.

The ratio of Compound III to Compound IV in the reaction medium is typically at least 3:1. The preponderance of the cis-isomer relative to the trans-isomer is the reverse of the isomer distribution attained in most prior art routes to DHCA.

Also surprisingly it has been found that the diastereomers represented by formula II exhibit different isomer distributions in this reaction. The major diastereomer produced from the oxazolidone represented by formula VIa corresponds to formula IIa

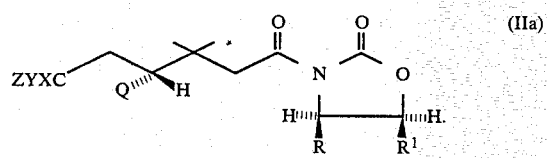
(IIa)

The major diastereomer produced from the oxazolidone corresponding to the enantiomer of Compound VIa can be represented by:

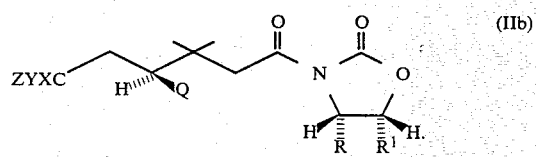
(IIb)

Both compounds IIa and IIb yield corresponding compounds of formulae III (cis) and IV (trans) in a ratio of 3:1. Nearly all of the cis-isomer derived from compound IIa is an amide precursor of L-cis-DHCA and essentially all of the trans-isomer is an amide precursor of D-trans-DHCA. Nearly all of the cis-isomer derived from compound IIb is an amide precursor of D-cis-DHCA, corresponding to formula IIIb, and essentially all of trans-isomer is an amide precursor of L-trans-DHCA.

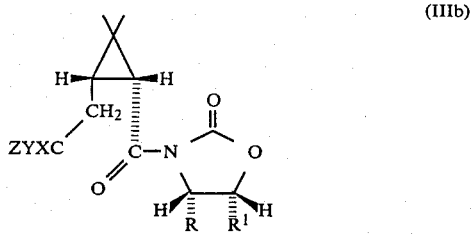

(IIIb)

The diastereomer of formulae IIa or IIb constitutes about 65 percent of the Compound II prepared by the method described hereinbefore.

The minor diastereomer represents about 35 percent of Compound II. The minor diastereomer derived from the oxazolidone VIa corresponds to the formula IIa -2:

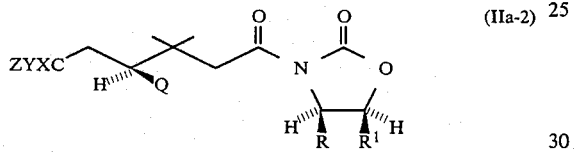

(IIa-2)

Compound IIa -2 yields the corresponding compounds of formulae III (cis) and IV (trans) in a ratio of up to about 9:1. Moreover, nearly all of the cis-isomer formed is the amide precursor of D-cis-DHCA; said precursor corresponds to a compound of formula IIIa -2.

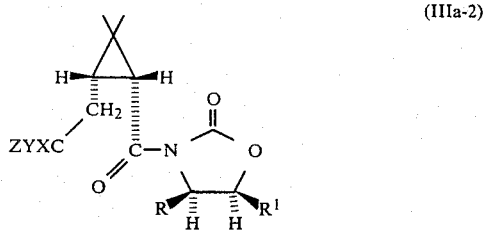

(IIIa-2)

The minor diastereomer derived from the enantiomer of oxazolidone VIa is primarily an intermediate for a precursor of L-cis-DHCA.

Inasmuch as insecticidal esters prepared from the D-cis enantiomer of DHCA are known to display superior activity relative to esters prepared from the other enantiomer, the novel Compounds IIb, IIIb, IIa -2 and IIIa -2 are of special interest. Of course, the diastereomeric mixture of Compounds IIa and IIa -2 or IIb and its diastereomer can be readily resolved by high-pressure liquid chromatography or other conventional techniques to yield preferred precursors of D-cis-DHCA.

Step (b)

In step (b) the compound of formula III optionally together with the compound of formula IV is reacted in a liquid medium to yield an acid or ester corresponding to Compound I. It is advantageous to employ a diluent in which the reactants from step (b) are soluble but which is inert to the reactants in step (b), so that the other reactants, optionally with additional diluent, can simply be introduced to the product mixture resulting from step (a). Alternatively, Compound III with or without IV can be isolated from the product mixture of step (a) by fractional distillation and then reacted in accordance with step (b).

The reaction mixture of step (b) should contain sufficient water to hydrolyze the amide moieties of Compounds III and IV if the corresponding acid is desired. In general, it is advantageous to employ a greater than stoichiometric amount of water to encourage the desired hydrolysis reaction to the acid; whereas the reaction medium should be essentially anhydrous if the ester is desired. It is generally desirable in any event for the reaction medium to contain sufficient quantities of a polar cosolvent, such as $C_1$ to $C_4$ alkanol, tetrahydrofuran and other cyclic ethers or dimethyl formamide or other polar aprotic solvents, to enhance the solubility of the reactants. Conveniently, the diluent contains from about 1 to about 50 percent of water or an alkanol and a remaining amount of cosolvent.

The concentration of the reactants in the reaction medium can operably vary over a wide range. However, total concentrations of from about 0.1 to about 1 molar of Compounds III and IV are generally convenient.

Generally, a base should be present in the aqueous medium to conduct dehydrohalogenation of the compound and to promote hydrolysis. Operable basic reagents include alkali and alkaline earth metal hydroxides and alkali metal alkoxides. Sodium and potassium hydroxide are preferred as basic reagents. Advantageously, a greater than stoichiometric quantity of the base is employed, with about a 10 to 500 mole percent excess being preferred.

It has been observed that cis-isomers are generally less readily hydrolyzed and dehydrohalogenated than the corresponding trans-isomers. It has been found in some instances that lithium methoxide will esterify the compound of formula III, but it is necessary to employ a stronger base, such as potassium hydroxide, to effect dehydrohalogenation and hydrolysis in good yield. See Example 7. In some embodiments, sequential treatment with a base, then an acid followed by a base, may provide an improved yield of product. See Example 5.

The reaction temperature is not critical so long as a practical reaction rate is maintained without any substantial deleterious effect on the product or reactants. Temperatures in the range from about 0° C. to temperatures at which refluxing occurs are generally convenient and advantageous.

The DHCA product can be separated from the reaction mixture by any convenient means known in the art. One preferred means for recovering the acid is to extract the product in an aqueous basic solution. The aqueous base is then acidified and extracted with methylene chloride. Finally, the solvent is distilled from the product residue. The DHCA can then be esterified in the conventional manner to yield insecticidal compounds.

The following examples are presented to illustrate the invention. Unless otherwise indicated all parts and percentages are by weight. "THF" is tetrahydrofuran; "DMF" is dimethyl formamide.

EXAMPLE 1

A sample of 3.17 grams (0.066 mole) of a 50% oil dispersion of NaH was washed free of oil with three 25 milliliters (ml) portions of hexane and then suspended in 70 ml of dry THF-DMF (1:1 by volume). The NaH was contacted at 20° C. with 5.22 grams (0.06 mole) of 2-oxazolidone added in portions over a period of 30 minutes. This reaction mixture was stirred at ambient temperature for 40 hours and then 8.80 grams (0.006 mole) of 3,3-dimethylpent-4-enoyl chloride was added dropwise over a period of 5 minutes. The reaction mixture was stirred at ambient temperatures for 28 hours and partitioned between cold saturated $NaHCO_3$ (aq) and $CH_2Cl_2$. The organic phase was separated and dried with $Na_2SO_4$.

The methylene chloride was distilled from the organic fraction to yield a yellow oil. High pressure liquid chromatography on silica gel eluting with ethyl acetate-hexane (1:3 by volume) gave 8.37 grams (71%) of Compound V wherein R and $R^1$ are each hydrogen as a yellow oil. The structure of this compound was confirmed by infrared spectroscopy, proton magnetic resonance analysis and elemental analysis. The elemental analysis found carbon, hydrogen and nitrogen contents of 60.69, 7.37 and 6.96 percent, respectively; one would predict for a $C_{10}H_{15}NO_3$ compound that C=60.90%, H=7.67% and N=7.10%.

EXAMPLE 2

A solution of 0.407 grams (0.0021 mole) of the compound isolated in Example 1 and $26 \times 10^{-6}$ liter (0.0020 mole) of $Fe(CO)_5$ in 1 ml of $CCl_4$ was heated at reflux for 26 hours. The reaction mixture was diluted with an equal volume of a mixture of $Et_2O$—$CH_2Cl_2$ (1:1 by volume) and filtered through a 3-inch column of silica gel eluting with $Et_2O$.

Evaporation and distillation at reduced pressure yielded 0.71 gram of a compound which slowly solidified on standing. This solid has a melting point of 61°–64° C. and was identified by conventional methods of analysis as corresponding to formula II, wherein R and $R^1$ are each —H and Q, X, Y and Z are each Cl. Elemental analysis found carbon, hydrogen and nitrogen in the following percentages, 37.39, 4.26 and 4.01; on a theoretical basis a $C_{11}H_{15}Cl_4NO_3$ compound should contain 37.64 percent carbon, 4.31 percent hydrogen and 3.99 percent nitrogen. The isolated yield was 97 percent of the theoretical yield.

EXAMPLE 3

To a suspension of 0.54 gram (0.011 mole) of 50% NaH in oil (washed free of oil with three 5 ml portions of hexane) in 10 ml of dry THF-DMF (1:1 by volume) was added at 20° C. a solution of 3.45 gram (0.0098 mole) of the compound isolated Example 2 in 7 ml of THF. A mildly exothermic reaction (temperature rose to 27° C.) and hydrogen evolution was observed. The reaction mixture was allowed to stir at ambient temperature for 48 hours and then was refluxed for 1 hour. The reaction mixture was cooled to room temperature and the excess NaH was reacted by dropwise addition of saturated $NH_4Cl$ (aq). The mixture was partitioned between $Et_2O$ and $H_2O$. The organic phase was separated and then dried with $Na_2SO_4$. The organic fraction was distilled to yield 2.80 g of amber oil. The ratio of cis:trans-isomers in this oil was determined to be 85:15.

Treatment of the oil via high-pressure liquid chromatography (HPLC) using silica gel and eluting with 25% ethyl acetate-hexane gave 1.57 g of a compound identified as corresponding to formula III wherein R and $R^1$ are both —H and Q, X, Y and Z are Cl, as a colorless solid. Recrystallization from benzene gave colorless plates having a melting point of 124° to 125° C. Elemental analysis found 41.64% of C, 4.53% of H and 4.44% of NO; theory would predict for a $C_{11}H_{14}Cl_3NO_3$ compound that C=42.00%, H=4.49% and N=4.45%.

Further elution from the liquid chromatographic column yielded 0.10 gram of a second compound, which was identified as corresponding to formula IV wherein R and $R^1$ are each —H and Q, X, Y and Z are each —Cl. Recrystallization from benzene yielded colorless plates having a melting point of 127° to 128.5° C. Elemental analysis indicated C=41.93%, H=4.41% and N=4.37%.

This example demonstrates that a preponderance of the cis-isomer is produced via the subject method.

EXAMPLE 4

A mixture of 1.57 grams (0.00498 mole) of the cis-isomer prepared in Example 3 and 0.245 gram (0.0102 mole) of NaOH in 10 ml of ethanol-$H_2O$ (1:1 by volume) was heated at reflux for 31 hours. The reaction mixture was then partitioned between diethyl ether and 10% KOH. The aqueous phase was separated and acidified to pH1 and extracted with $CH_2Cl_2$. The $CH_2Cl_2$ extract was dried with $MgSO_4$ and evaporated to yield 0.20 g of a colorless oil which crystallized on standing. This product was confirmed by proton magnetic resonance to correspond to formula I, wherein X and Y are each Cl and $R^3$ is H.

EXAMPLE 5

An improved method of hydrolyzing the cis-isomer prepared in Example 3 was developed. A solution of 2.22 grams (0.00706 mole) of this cis-isomer in 35 ml of tetrahydrofuran-ethanol (2:3 by volume) was treated in 2.1 ml (0.015 mole) of 7N KOH for 24 hours at 20° C. Volatile components of the resulting mixture were removed by distillation at reduced pressure. The white solid residue was suspended in 35 ml of 3N hydrochloric acid and heated at reflux for 4 hours.

The reaction mixture was extracted with three portions of $CH_2Cl_2$ and dried with $MgSO_4$ for 1 minute. Distillation of the $CH_2Cl_2$ under reduced pressure yielded an amber oil. The oil was dissolved in 15 ml of ethanol and 5 ml of KOH was added. The resulting basic reaction medium was stirred at 20° C. for 30 minutes and heated at reflux for 4 hours.

The reaction mixture was distilled to remove any ethanol. The residue was partitioned between water and diethyl ether. The aqueous phase was separated and hydrochloric acid was added to adjust the pH to 3. The acidified aqueous phase was extracted three times with $CH_2Cl_2$. The combined $CH_2Cl_2$ extracts were dried with $Na_2SO_4$ and volatile materials removed by distillation to yield 1.03 grams of a pale yellow solid. The product was confirmed by proton magnetic resonance to correspond to formula I, wherein X and Y are each —Cl and $R^3$ is H.

The crude product was recrystallized in hexane to yield a total 0.911 gram of essentially pure product in two crops. This represents a 62 percent overall yield based on the cis-isomer used as a starting material.

EXAMPLE 6

In accordance with the method described in U.S. Pat. No. 3,935,280, (R)-valinol was prepared from (R)-valine in 65 percent yield. The product was a hygroscopic solid having a melting point of 31.5°–33° C.

To 340 ml of toluene was added 21.3 grams (0.206 mole) of (R)-valinol and 37.6 grams (0.232 mole) of carbonyldiimidazole. This mixture was heated at reflux for 18 hours and then cooled to ambient temperature. The reaction mixture was then partitioned between $CH_2Cl_2$ and dilute aqueous HCl. The aqueous layer was separated and extracted four times with $CH_2Cl_2$. The combined $CH_2Cl_2$ extracts and separated $CH_2Cl_2$ phase were dried with $Na_2SO_4$ and distilled under reduced pressure to remove volatiles. Recrystallization of the residue in diethyl ether yielded 9.73 grams of a colorless, crystalline solid having a melting point of 70°–72° C. This solid was identified by conventional techniques as a 2-oxazolidone corresponding to the formula:

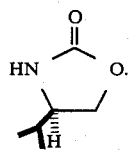

The theoretical elemental analysis for $C_6H_{11}NO_2$ is C=55.80%, H=8.58% and N=10.84%; whereas it was found C=56.05%, H=8.43% and N=10.95%.

To 25 ml of THF was added 6.00 grams (0.0463 mole) of the above-identified 2-oxazolidone. This solution was added dropwise to 2.44 grams (0.051 mole) of NaH (derived from an oil dispersion but washed free of oil with hexane) in 35 ml of dry THF. This mixture was then cooled in an icebath and 6.79 grams (0.0463 mole) of 3,3-dimethylpent-4-enoyl chloride was added dropwise. The mixture was stirred at ambient temperatures for 24 hours and then partitioned between diethyl ether and saturated aqueous $NaHCO_3$. The diethyl ether was dried with $NaSO_4$ and the volatiles distilled to leave a pale yellow liquid. Kugelrohr distillation of the liquid yielded 9.47 grams of a colorless liquid. This liquid was identified by conventional analytical techniques to correspond to the formula X

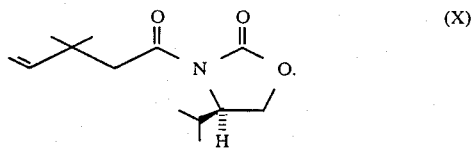

The theoretical elemental analysis for $C_{13}H_{21}NO_3$ is C=65.24%, H=8.85% and N=5.85%, while it was observed that C=65.36%, H=8.86% and N=5.85%.

To 13.6 ml of $CCl_4$ was added 5.42 grams (0.0227 mole) of compound X and 0.35 ml of $Fe(CO)_5$. This solution was refluxed for 6 hours and then cooled to room temperature. The reaction mixture was filtered through a column packed with alumina and the column washed with $CH_2Cl_2$. The combined filtrate was evaporated at reduced pressure to remove volatiles leaving a yellow oil. Treatment of the oil via HPLC using silica gel and eluting with an ethyl acetate and hexane mixture (ratio of 1:9 by volume) gave 7.67 grams of a yellow oil. It was determined by conventional techniques that this oil was a 60:40 mixture of diastereomers corresponding to formulae IIa and IIa-2, respectively, wherein Q, X, Y and Z are each —Cl, R is isopropyl and R' is —H.

These two diastereomers were separated by a careful repetition of the HPLC procedure in which the sampling of each compound was initiated after their respective detector response curves reached the inflection points on their upward slope and discontinued at the inflection point on its downward slope. The diastereomers were then separately recrystallized from hexane.

The isolated diastereomer corresponding to formula IIa was a colorless solid having a melting point of 70.5°–72° C. The theoretical elemental analysis for $C_{14}H_{21}NO_3Cl_4$ is C=42.77%, H=5.38%, N=3.56% and the actual values were C=42.91%, H=5.39% and N=3.62%. Its stereochemistry was confirmed by single crystal X-ray analysis.

The isolated diastereomer corresponding to formula IIa-2 was a colorless crystalline solid having a melting point of 69°–70° C. Its elemental analysis was C=42.77%, H=5.31% and N=3.51%.

EXAMPLE 7

Lithium methoxide was prepared by addition of 4.44 ml. (0.006 Mole) of 1.35 molar n-butyllithium in hexane to a mixture of 4 ml of THF and 4 ml of anhydrous methanol at 5° C. over a period of 10 minutes. This mixture was stirred for 10 minutes and then 0.629 gram (0.002 mole) of a compound of formula III, wherein X, Y and Z are each —Cl and R and $R^1$ are each —H, was added. The reaction mixture was warmed to ambient temperature and stirred for 48 hours.

This reaction mixture was partitioned between diethyl ether and an aqueous solution buffered to a pH of 7. The organic phase was separated and dried with $Na_2SO_4$. The diethyl ether was distilled from the mixture at atmospheric pressure and the remaining volatiles were distilled at reduced pressure (80° C., 0.5 millimeter of Hg). The residue was 0.374 grams of a colorless liquid. The structure of this product was confirmed by conventional analytical techniques to correspond to an ester of the formula

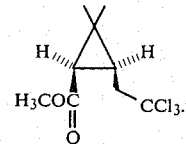

A solution of 0.273 gram (0.001 mole) of the above-identified ester in 1.5 ml of ethanol was combined with 0.36 ml (0.0025 mole) of 7.0 normal aqueous potassium hydroxide. This mixture was stirred at ambient temperatures for 30 minutes, then refluxed for 5 hours. The ethanol was removed by evaporation and the residue partitioned between diethyl ether and water. The aqueous phase was separated, acidified with a small quantity of HCl and extracted twice with $CH_2Cl_2$. The combined $CH_2Cl_2$ extracts and diethyl ether phase were dried with $NaSO_4$ and the volatiles evaporated to yield 0.220 gram of a pale yellow solid. This solid had a melting point of 78°–83° C. The structure of this product was confirmed by conventional analytical techniques to correspond to the formula I wherein $R^3$ is —H and X and Y are each —Cl.

EXAMPLE 8

To 0.35 gram (0.0071 mole) of NaH washed free of oil with hexane and suspended in 14 ml of dry THF-DMF (3:1 by volume) was added 2.56 grams (0.0065 mole) of a compound corresponding to formula IIa-2, wherein Q, X, Y and Z are each Cl, $R^1$ is H and R is isopropyl.

The mixture was stirred for 48 hours at ambient temperature and then partitioned between diethyl ether and aqueous NH₄Cl. The organic phase was separated, dried with Na₂SO₄ and evaporated at reduced pressure. The colorless solid residue was analyzed by conventional techniques and was found to contain 88% of the D-cis isomer (corresponding to formula IIIa-2), 9% of the L-trans isomer, 2% of the L-cis isomer and 1% of the D-trans isomer.

Purification of the solid product via HPLC isolated 1.95 grams of a colorless solid having a melting point of 112.5°–116.5° C. The theoretical elemental analysis was C=47.14%, H=5.65%, N=3.93% and Cl=29.82% and the actual values were C=47.24%, H=5.54%, N=3.83% and Cl=30.06%.

EXAMPLE 9

A compound corresponding to formula IIa, wherein Q, X, Y and Z are Cl, R' is H and R is isopropyl is reacted in a manner similar to compound IIa-2 in Example 8. The resulting solid product was determined to contain 75% of the L-cis and 22% of the D-trans isomer.

What is claimed is:

1. A compound corresponding to formula II

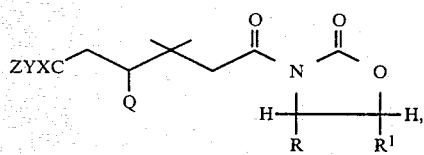
(II)

wherein X and Y are each independently halo, $C_1$ to $C_4$ perhaloalkyl, $C_1$ to $C_4$ alkyl, —CN, —CO₂R" or —CONR"₂, wherein R" at each occurrence is $C_1$ to $C_4$ alkyl, with the proviso that at least one of X or Y is halo or perhaloalkyl, Q and Z are each independently —Br or —Cl, and R and R¹ are each independently hydrogen, $C_1$ to $C_4$ alkyl, phenyl, benzyl or —CH₂CH₂SCH₃.

2. The compound as described in claim 1 wherein said compound is predominantly the diastereomer corresponding to the formula

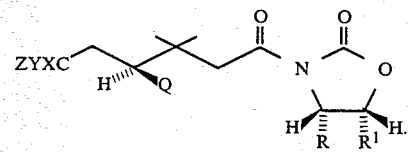

3. The compounds as described in claim 1 wherein at least one of X or Y is halo and the other is halo or —CF₃.

4. The compounds as described in claim 2 wherein at least one of X or Y is halo and the other is halo or —CF₃.

5. The compounds as described in claim 1, wherein X and Y are each independently —Cl or —Br.

6. The compounds as described in claim 2 wherein X and Y are each independently —Cl or —Br.

7. The compounds as described in claim 5 wherein R is a $C_1$ to $C_4$ alkyl and R¹ is —H or R is —CH₃ and R¹ is phenyl.

8. The compounds as described in claim 6 wherein R is a $C_1$ to $C_4$ alkyl and R¹ is —H or R is —CH₃ and R¹ is phenyl.

9. The compounds as described in claim 7 wherein X, Y and Z are each —Cl.

10. The compounds as described in claim 8 wherein X, Y and Z are each —Cl.

11. The compound as described in claim 1 wherein said compound is predominantly the diastereomer corresponding to the formula

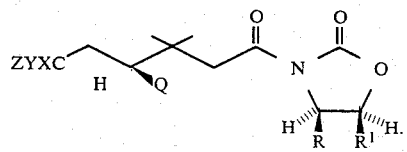

12. The compound as described in claim 11 wherein X, Y, Z and Q are each —Cl, R is a $C_1$ to $C_4$ alkyl and R¹ is —H.

13. The compound as described in claim 11 wherein X, Y, Z and Q are each —Cl, R is methyl and R¹ is phenyl.

14. The compound as described in claim 1 wherein at least one of X or Y is halo.

15. The compound as described in claim 14 wherein R is a $C_1$ to $C_4$ alkyl and R¹ is —H or R is —CH₃ and R¹ is phenyl.

16. The compounds as described in claim 2 wherein at least one of X or Y is halo.

17. A compound corresponding to the formula V

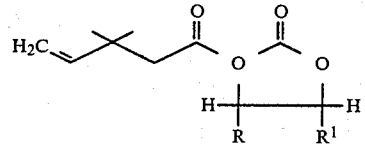
(V)

wherein R and R¹ are each independently —H, $C_1$ to $C_4$ alkyl, phenyl, benzyl or —CH₂CH₂SCH₃.

* * * * *